United States Patent [19]

Zurolo et al.

[11] 4,003,704

[45] Jan. 18, 1977

[54] MEDICAL EXAMINATION TABLE COVER SYSTEM HAVING STERILIZING MEANS THEREFOR

[75] Inventors: Gabriel J. Zurolo; Elmer G. Bull, both of Hamden, Conn.

[73] Assignee: Mark Medical Supply, Inc., New Haven, Conn.

[22] Filed: Mar. 26, 1975

[21] Appl. No.: 562,220

[52] U.S. Cl. .................................. 21/91; 21/102 R; 21/DIG. 2; 250/455; 250/492 R; 269/322; 269/323; 269/324; 269/325; 269/326

[51] Int. Cl.² ..................... A61G 13/00; A61L 3/00

[58] Field of Search ........... 21/81, 91, 102 R, 54 R, 21/DIG. 2; 250/453–456, 492 R; 128/376, 377; 269/322–326; 297/221; 5/317 R; 312/209

[56] References Cited

UNITED STATES PATENTS

| | | | |
|---|---|---|---|
| 1,881,310 | 10/1932 | Coatsworth | 21/91 X |
| 1,981,954 | 11/1934 | Heller | 21/91 X |
| 2,609,623 | 9/1952 | Miller | 21/81 UX |
| 3,110,974 | 11/1963 | Paullus et al. | 21/102 R UX |
| 3,466,679 | 9/1969 | Hess | 5/317 R |
| 3,810,263 | 5/1974 | Taylor et al. | 269/323 X |

*Primary Examiner*—Morris O. Wolk
*Assistant Examiner*—Bradley Garris
*Attorney, Agent, or Firm*—DeLio and Montgomery

[57] ABSTRACT

A medical examination table cover system wherein an endless web of sanitary cover material having a length several times the unit length of the table to be covered is guided on a course such that an area which has been used is moved into a sterilizing zone and retained there long enough for effective sterilization, while other areas are successively used and, in turn, subjected to sterilization; the movement of the web being effected by a motor controlled to advance the web by one unit length at a time, and the sterilization being effected by irradiation by fluorescent germicidal lamps.

8 Claims, 6 Drawing Figures

MEDICAL EXAMINATION TABLE COVER SYSTEM HAVING STERILIZING MEANS THEREFOR

This invention relates to a medical examination table cover system comprising an endless web of sanitary cover material having a length several times the unit length of the table surface to be covered, with means for guiding the web on a course such that an area which has been used can be moved into a sterilizing zone and retained therein long enough for effective sterilization while other areas are successively used and, in turn, advanced to the sterilizing zone; the movement of the web is effected by a motor controlled to advance the web step by step one unit length at a time; the sterilization is effected by irradiation by fluorescent germicidal lamps.

Examination tables commonly used in doctor's offices, hospitals and the like are generally flat couch-like devices with a single thinly padded surface about five feet long or with a divided surface, one part constituting a seat and the other part being hinged so that it can be raised to form a back support for a patient in a reclining seated position, said parts being supported on a pedestal or other suitable base with or without a step at the "foot" end. For sanitary reasons a paper covering is normally provided, the paper being carried on a roll at one end of the table so that a suitable length can be pulled across the table for use by a patient (sitting or lying on the table) and then discarded as a fresh length of paper is drawn from the roll to receive the next patient. Such disposable paper covers represented an advance in the art over the elongated textile sheet, drawn from a supply roll to a take-up roll, as shown in Steiner U.S. Pat. No. 1,877,610, and the latter was an improvement over the use of separate loose bed sheets. Paper table covers, however, present a serious disposal problem; the paper is fairly heavy and each five foot length of it has sufficient bulk to require a large receptacle for a busy office. Each discarded section is, or may be, more or less contaminated by contact with a patient's body and/or clothing, so that careful handling is required.

It is an object of the present invention to provide a table cover system which includes an endless web of sterilizable cover material and means for advancing it across the surface of an examination table, whereby a sterile unit length of the material can be provided for the use of each patient.

It is a further object of the invention to provide such an endless web having an extended length, means for guiding part of the web along a zig-zag course within the table and means for sterilizing the web as it is guided along such course.

It is another object of the invention to provide such an endless web of impervious non-absorbent material, adapted to be wiped clean if necessary.

It is a still further object of the invention to provide web advancing means with controls for automatically advancing and withdrawing a unit length of the web upon each actuation of said means.

It is yet another object of the invention to provide certain improvements in the form, construction and arrangement of the several parts whereby the above named and other objects may effectively be attained.

The invention accordingly comprises the features of construction, combination of elements, and arrangement of parts which will be exemplified in the construction hereinafter set forth, and the scope of the invention will be indicated in the claims.

A practical embodiment of the invention is shown in the accompanying drawings, wherein.

Figure 1:
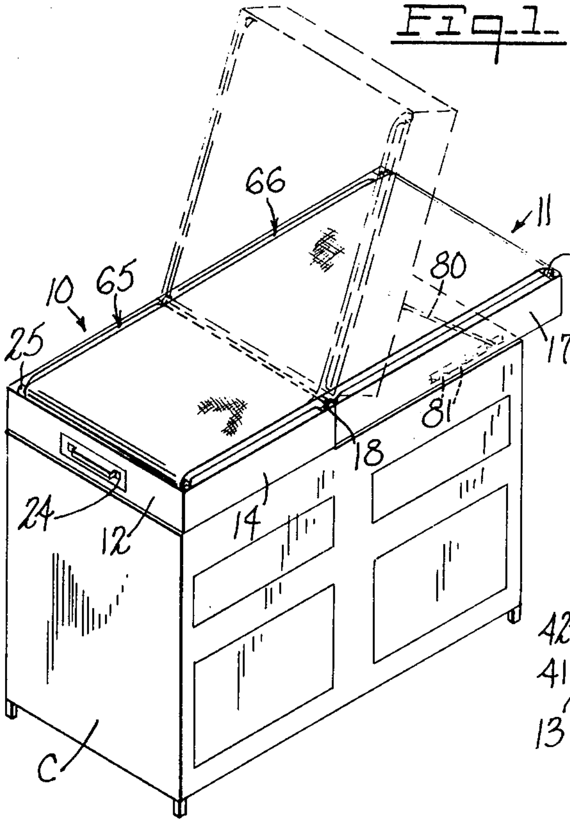
FIG. 1 is an isometric projection of an examination table according to the invention, on a conventional support, the raised position of the back rest portion being shown in broken lines.

Referring to the drawings, the table comprises a seat portion 10 and a back portion 11, each being in the form of a deep tray, the seat portion having end and side walls 12, 13, 14 and the back portion having end and side walls 15, 16, 17. The respective adjacent inner ends are open and the portions are hinged together at 18 for relative pivotal movement around a horizontal axis adjacent the upper corners of said inner ends.

The examination table is adapted to be mounted on a suitable support which may be a cabinet C, as shown, or a pedestal stand or other equivalent device. The seat portion 10 should be fastened to the top of the support in any secure manner, as by means of bolts or the like, not shown. The seat portion may conveniently be equipped with a drawer 24, in the front end wall 12, as is customary.

The seat portion 10 is provided with an idler roll 25 journalled in blocks 26, 27 on the side walls 13, 14 just inside the upper edge of end wall 12. At the hinged end of the seat portion the walls 13, 14 are provided with bearing blocks 28, 29 which project slightly beyond the ends of the walls. The feed roller 30 is journalled in said blocks 28, 29 in a position directly below the hinge 18 and small idler rolls 31, 32 are also journalled in said blocks just above the feed roller and below the upper edges of the side walls.

The feed roller 30 may suitably be driven by the motor M through a worm drive 33 and gears 34 and 35, the latter being fixed on the axle 36 of the roller, adjacent one end thereof. At its other end the roller is provided with an eccentrically mounted pin 37 adapted to engage in the slots 38 of the star wheel 39 (journalled on a stub axle 40 in the block 28) which carries a cam 41 on its periphery in a position to actuate the switch 42 through the cam follower 43.

The electrical system for the table includes the power switch 45, motor start button 46, lamp control and timer 47 and relay 48, with suitable connections to the motor and to the lamps (described below).

The back portion 11 of the table is provided with an idler roller 49 journalled in bearing blocks 51, 52 on the side walls 16, 17 just inside the upper edge of end wall 15 and another idler roller 50 is mounted below the roller 49 near the bottom of wall 15. Near the hinged end of the back portion the walls 16, 17 are provided with bearing blocks 53, 54, and a plurality of additional idler rolls 55 (four being shown) are journalled in blocks 51, 52 with a like number of rolls 56 being journalled in blocks 53, 54.

Fluorescent germicidal lamps 60, 61 are mounted within the back portion 11, near and parallel to the side walls 16, 17, these lamps being connected in the electrical system through the lamp timer and control 47, whereby the interior of back portion 11 constitutes a "sterilization chamber".

The open tops of the seat and back portions 10 and 11 are covered by rectangular pads 65, 66, each comprising a rigid backing piece of plywood 67 or the like covered by a facing of plastic sheet or fabric 68 over a somewhat resilient layer of padding 69. The pads may be retained in place by means of clips 70 engaging a flange 17' along the top edge of the side wall, or in other convenient manners.

The table cover is an endless web 75 of impermeable fabric, preferably plastic or plastic-treated textile and relatively non-stretchable. It is disposed on a course which lies across the upper surfaces of the pads 65, 66 and around the idler rolls 25 and 49 at each end, being advanced toward the roll 25 by the feed roller 30. The path of the web around rolls 31 and 32 and the feed roller 30 is inverted omega-shaped to insure good driving contact throughout most of the periphery of the feed roller, the surface of which is preferably clad with rubber or an equivalent friction covering. From the roll 49 the web passes down around roll 50 and then follows a serpentine course, back and forth around the rolls 56 and 55 until reaching the uppermost roll 55 from which it goes to the roll 32. The number and disposition of the rolls 55, 56 is preferably such that the length of the web traversing said rolls is several times the distance across the top of the table between rolls 25 and 49. The diameter of feed roller 30 is such that a given number of revolutions thereof (e.g., five) will move all the exposed length of the cover from its position on top of the table to a position within the back portion 11, traversing the rolls 50, 56 and 55, while an equal length of cover material is advanced from the feed roller, past roll 25 and into exposed position.

In operation, the examination table, covered as described by a clean length of cover material, is used by a patient who may sit on the seat portion or lie on both portions during a routine examination. After such use of the table and in preparation for the next patient, any visible soiling of the cover is noted and wiped away. The power switch 45 is turned on to render all electrical units operative, and the lamp control 47 is also turned on to activate the germicidal lamps 60, 61. The motor start button 46 is pushed, starting the motor M and setting the relay 48, in condition for stopping the motor in response to activation of switch 42. The motor drives the feed roller, each revolution of which causes the pin 37 to advance the star wheel 39 one-fifth of a revolution (as shown); after five revolutions of the feed roller the cam 41 on the star wheel hits the cam follower 43 and the switch 42 causes the relay to stop the motor.

By this operation the exposed length of the table cover is drawn into the sterilization chamber within the seat portion 11 and becomes subjected to the action of the germicidal lamps. As further examinations are conducted, additional exposed lengths of cover material are successively drawn into the sterilization chamber. Each examination normally takes ten to thirty minutes, and there is also usually a substantial interval between examinations so that, if the lamps remain turned on, a first exposed length of the cover may be subjected to germicidal lamp radiation for at least one hour and perhaps much longer. Disposition of the lamps along each side of the chamber, parallel to the edges of the web, assures good distribution of the radiations and efficient treatment of all parts of the web. In the form shown, the endless web 75 has a total length equal to about five times the length of the table so that at least three unit lengths are being irradiated at all times (allowing for that portion of the course from roll 32 to roll 25).

The feed roller 30 is arranged to run in contact with the back of the cover material so that it can never become soiled even if the face of the cover should not be wiped clean.

Figure 5:
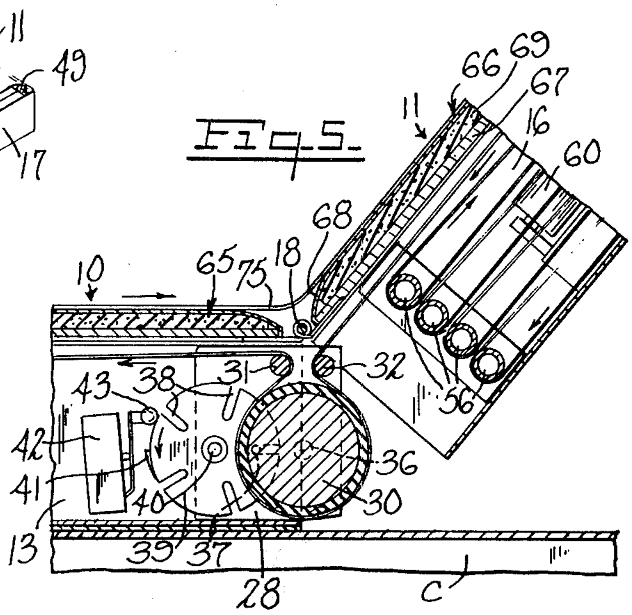
FIG. 5 represents a detail vertical section, like FIG. 3, showing the hinge with the adjacent back rest portion in raised position.
Figure 4:
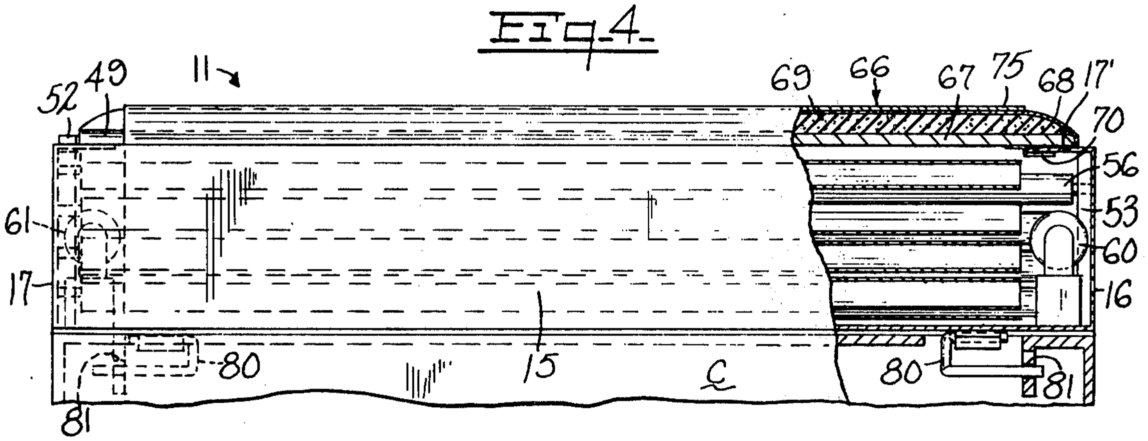
FIG. 4 represents an end elevation of the table as viewed from the right of FIG. 3, parts being broken away and in section.
Figure 6:
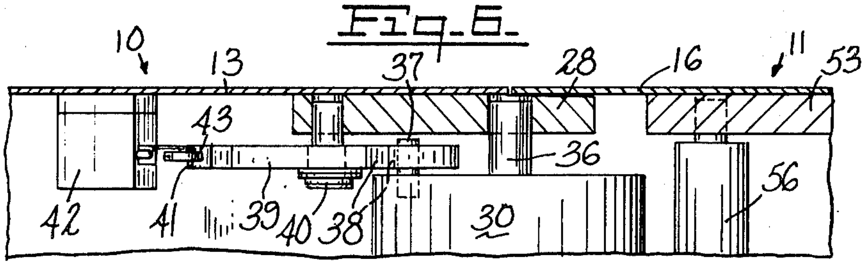
FIG. 6 represents a detail horizontal section on the line VI—VI of FIG. 3 showing a top plan view of the star wheel drive.
Figure 2:
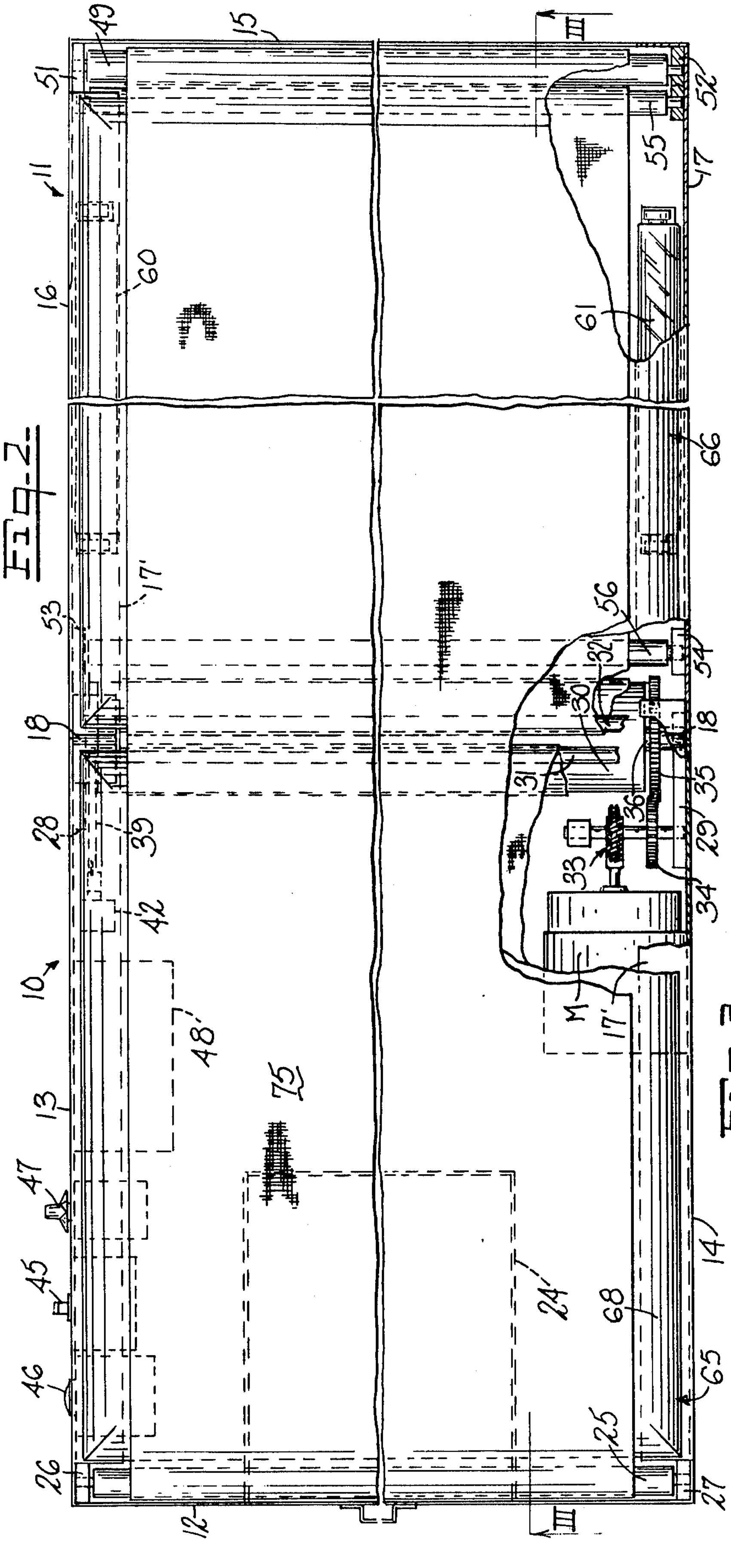
FIG. 2 represents a top plan view of the table, parts being broken away to show interior details.
Figure 3:
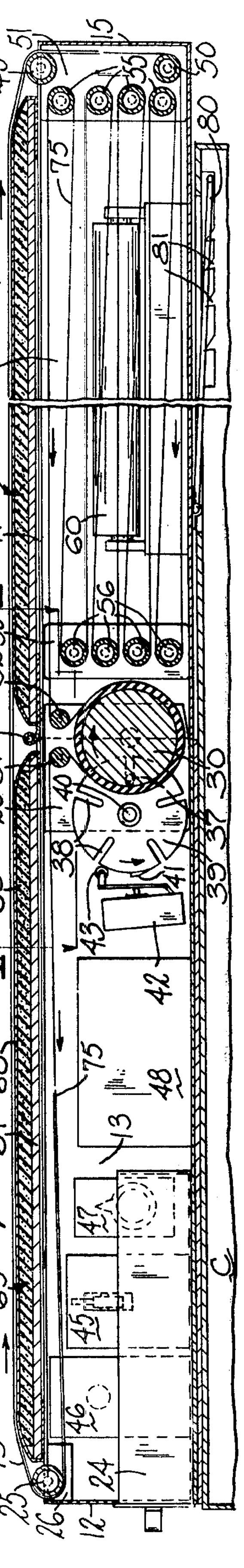
FIG. 3 represents a vertical longitudinal section on the line III—III of FIG. 2.

Many examinations are conducted with the table remaining flat and the patient either sitting up on the seat portion or lying down. Provision is made, however, for raising the back portion to form a reclining support, as shown in broken lines in FIG. 1, the back being held in raised position by any customary form of releasable brace, indicated conventionally as a rod 80 the lower end of which can be engaged, in various adjusted positions, with stops 81 on the table support (FIGS. 1, 3 and 4). The hinging movement of the back portion has no appreciable stretching or slackening effect on the web 75, as will be appreciated from FIG. 5.

If desired or advisable, means may be provided for ventilation of the sterilization chamber.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

What we claim is:

1. A medical examination table cover system comprising an examination table having a patient-supporting upper surface and an enclosed chamber below said upper surface, an endless web of cover material, first means for guiding said web to cause a unit length thereof to lie in a position exposed on said upper surface, additional means for guiding other lengths of said web through said enclosed chamber, means for subjecting said other lengths to a sterilization procedure in said chamber, and feed means for moving the exposed unit length of the web from said upper surface into said chamber and another length of said web into said exposed position.

2. A medical examination table cover system according to claim 1, wherein said other lengths of said web are several times longer than said unit length.

3. A medical examination table cover system according to claim 1 wherein the table comprises a seat portion and a back portion, said portions being hinged together and each having a patient-supporting surface and an enclosed individual chamber below each said surface, the first web guiding means comprising two rollers journalled at opposite ends of said table portions to define the unit length of cover material, the additional guiding means comprising a plurality of rollers journalled within the back portion and the feed means comprising a feed roller journalled in the seat portion and driving means for said feed roller.

4. A medical examination table cover system according to claim 1 wherein the feed means includes a feed roller, a motor for driving said feed roller, and motor control elements for starting said motor and, after the feed roller has advanced the web a distance at least equal to said exposed unit length, for stopping said motor.

5. A medical examination table cover system according to claim 4 wherein said motor control elements include a star wheel for indicating the advancements to the web a distance at least equal to said exposed unit length and means on the feed roller for actuating the star wheel.

6. A medical examination table cover system according to claim 1 wherein said means for guiding other lengths of said web includes a plurality of rollers in said chamber, so disposed as to define a serpentine course of travel for said web.

7. A medical examination table cover system according to claim 6 wherein the sterilization means comprise fluorescent germicidal lamps.

8. A medical examination table cover system according to claim 7 wherein the lamps are disposed lengthwise of the chamber adjacent opposite edges of the web.

* * * * *